United States Patent [19]

Martinez-Alvarez et al.

[11] 3,979,382

[45] Sept. 7, 1976

[54] DICHLOROCYANURATE SILVER COMPLEXES

[75] Inventors: Francisco Martinez-Alvarez; Antonio Gamero Briones, both of Barcelona; Enrique Dominguez Buron, Badalona, all of Spain

[73] Assignee: Sociedad Anonima Cros, Barcelona, Spain

[22] Filed: Nov. 11, 1974

[21] Appl. No.: 522,894

[30] Foreign Application Priority Data
Nov. 15, 1973 Spain .................................. 420561

[52] U.S. Cl. .................................. 260/242; 71/67; 424/245
[51] Int. Cl.$^2$ ........................................ C07D 251/36
[58] Field of Search ........................ 260/242; 71/67; 424/245

[56] References Cited
UNITED STATES PATENTS

| | | | |
|---|---|---|---|
| 3,055,889 | 9/1962 | Marek | 260/242 |
| 3,205,229 | 9/1965 | Matzner | 260/242 |

*Primary Examiner*—Harry I. Moatz
*Attorney, Agent, or Firm*—Woodhams, Blanchard and Flynn

[57] ABSTRACT

Dichlorocyanurate silver complexes of the formulas $(Ag)_1(A)_1(Z)_2$ and $(Ag)_2(B)_1(Z)_4$ wherein Z is the dichlorocyanurate radical $(C_3N_3O_2Cl_2)$-, A is an alkali metal and B is an alkaline earth metal. The compounds possess antibacterial activity.

7 Claims, No Drawings

DICHLOROCYANURATE SILVER COMPLEXES

BACKGROUND OF THE INVENTION

1. Field of the Invention

This invention relates to the preparation of novel chlorine-containing compounds, which also contain combined silver. These compounds are of special interest in those applications where it is desired to obtain the bactericidal effects of chlorine in combination with the effect of silver.

2. Description of the Prior Art

Dichlorocyanurate complexes are disclosed in the following patents:

E. A. Matzner, U.S. Pat. No. 3,287,359;
E. A. Matzner, U.S. Pat. No. 3,294,690;
R. W. Marek, U.S. Pat. No. 3,115,493;
R. W. Marek, U.S. Pat. No. 3,094,525;
R. W. Marek, German Pat. No. 1,131,217.

SUMMARY OF THE INVENTION

This invention provides novel dichlorocyanurate silver complexes of the formulas: $(Ag)_1(A)_1(Z)_2$ and $(Ag)_2(B_1)(Z)_4$, wherein Z is the dichlorocyanurate radical $(C_3N_3O_3Cl_2)$-, of the structure

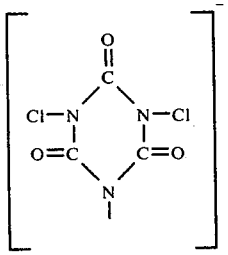

and A is an alkali metal, preferably sodium or potassium, and B is an alkaline earth metal, preferably calcium, barium or magnesium.

The novel compounds to which this invention relates can be readily prepared by reacting, in an inert solvent solution, alkali salts or alkaline earth metal salts of dichlorocyanuric acid with a soluble silver salt. The solvent employed preferably is water because the novel compounds readily precipitate therein. The reaction can advantageously be carried out at a temperature in the range of 0° to 60°C, preferably at ambient temperature (20°–25°C), although the reaction temperature is not critical. The pH of the reaction medium is controlled to be in the range of from 3 to 7. The reactant concentrations are not critical, except to the extent that they must be sufficient to insure that the novel compounds preciptitate from the solution. The molar ratios of the reactants are not critical because the desired novel compounds will form until the reactant present in the lesser stoichiometric amount is fully reacted. It is preferred to employ molar ratios of dichlorocyanuric acid salt/silver salt of about 2/1 when complexes of the above formula $(Ag)_1(A)_1(Z)_2$ are to be formed, and to employ molar ratios of dichlorocyanuric acid salt/silver salt of about 1/1 when complexes of the above formula $((Ag)_2(B_1)(Z)_4$ are to be formed.

The novel compounds according to the invention are highly stable and exhibit much higher levels of active chlorine concentration over an extended period of time, in comparison with simple salts of dichlorocyanuric acid.

The solubilities of the novel compounds of the invention, in water, are very low. For example, in the case of the compound of the formula $(Ag)_1(K)_1(Z)_2$, wherein Z is as defined above, its solubility in water at 20°C is less than 0.001 percent. Their high stability and low solubility, as well as their bactericidal, fungicidal and algicidal effects, make the compounds according to the invention commercially useful for various purposes such as when it is desired to employ a fixed bed of the compounds for continuous treatment of a flowing aqueous stream. Therefore the compounds according to the invention possess great usefulness in controlling ferruginous algae and bacteria, to avoid incrustation and corrosion in cooling towers, as well as in purifying water used in industrial processes in which the development of algae and bacteria is a problem, such as in the manufacturing of paper.

The compounds according to the invention can be used in the fixed bed form, either by themselves or they can be deposited on an inert support or carrier substance such as Celite, kieselguhr, etc. The presence of such support substance does not decrease their biologic activity; on the contrary, the contact of the compound with the water to be treated is improved owing to an increase of its specific surface. In order to obtain a better distribution of the active compound on the support surface, it is preferred to form the compound, according to the invention, by precipitation in situ on the carrier substance, by adding a soluble silver salt to a suspension of the carrier substance in an aqueous solution of alkali metal or alkaline earth metal salts of dichlorocyanuric acid, thereby to precipitate on the carrier substance a compound according to the present invention.

From infrared spectroscope studies and conventional analytical methods, it has been proposed (F. Martinez et al, Third International Symposium on Polyhalogen Compounds, October, 1973, Barcelona, Spain) that these novel compounds have the following structures:

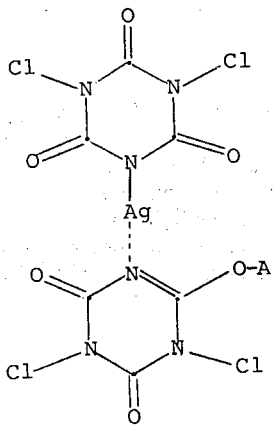

I and

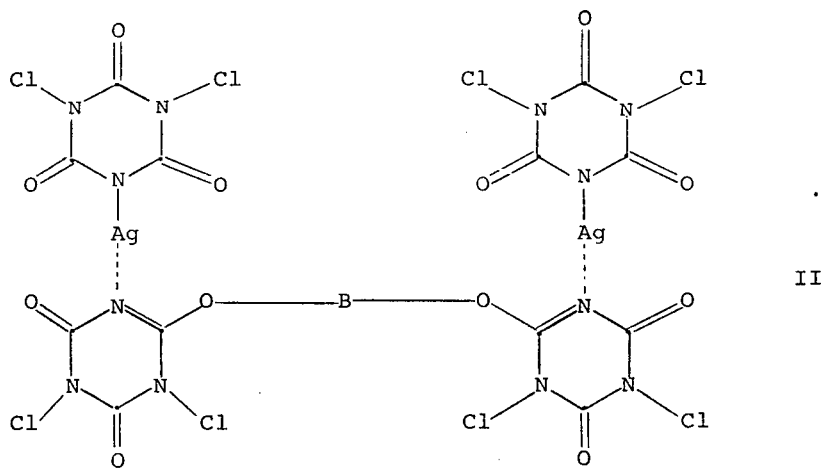

II

| Time | Starting Concentration E. Coli cells/ml. | Sodium dichlorocyanurate % killed | $(Ag)_1(K)_1(Z)_2$ % killed |
| --- | --- | --- | --- |
| 15 minutes | $4.2 \times 10^8$ | 99.2 | 100 |
| 2 days | | 100 | 100 |
| 3 days* | $4.2 \times 10^8$ | — | — |
| 5 days | | 100 | 100 |
| 6 days* | $4.2 \times 10^8$ | — | — |
| 8 days | | 88.0 | 100 |
| 22 days | | 74.2 | 100 |
| 26 days* | $4.2 \times 10^8$ | — | — |
| 27 days | | — | 100 |
| 44 days* | $4.2 \times 10^8$ | — | — |
| 48 days | | — | 99.1 |
| 50 days* | $4.2 \times 10^8$ | — | — |
| 52 days | | — | 99.9 |
| 58 days | | — | 97.3 |
| 60 days | | — | 91.9 |

*At the 3, 6, 26, 44 and 50$^{th}$ days, the cultivation media containing the respective salts were inoculated with further quantities of E. Coli to restore the concentration thereof to the initial value of $4.2 \times 10^8$ cells/ml.

wherein
A is an alkali metal, preferably sodium or potassium, and B is an alkaline earth metal, preferably calcium, barium or magnesium.

The novel compounds of formula $(Ag)_1(A)_1(Z)_2$, (I), according to this invention do not form hydrates, that is, they are obtained only in anhydrous form. The novel compounds of formula $(Ag)_2(B)_1(Z)_4$, II, can be obtained in either the hydrate or anhydrous forms.

The novel compounds according to this invention possess a highly persistent activity against bacteria which is surprisingly better than the activity of simple salts of dichlorocyanuric acid. For example, the following table compares the bactericidal effects obtained using sodium dichlorocyanurate and a compound of the formula $(Ag)_1(K)_1(Z)_2$ according to this invention, against E. Coli. The amounts of the compounds incorporated in the cultivation medium in both cases, was 50 ppm.

The persistency of the silver potassium dichlorocyanurate is approximately nine times as great as the corresponding sodium salt.

The preparation of compounds according to this invention is further described by reference to the following illustrative examples.

EXAMPLE 1

$(Ag)_1(K)_1(Z)_2$

In a vessel containing 9.4 g (0.04 moles) of potassium dichlorocyanurate and 200 ml. of water, there was added with stirring 3.4 g (0.02 moles) of silver nitrate dissolved in 100 ml. of water. There appeared instantaneously a white precipitate which was filtered to give 17.0 g of a wet product. This product was dried at 50°C and there was obtained 10.2 g (yield: 94.26% based on silver) of a white crystalline solid.

Analysis

Calculated for $(Ag)_1(K)_1(C_3N_3O_2Cl_2)_2$

Available chlorine: 52.43%
Ag : 19.94%
K : 7.23%

Found

Available chlorine: 52.15%
Ag : 20.58%
K : 7.24%

EXAMPLE 2

$(Ag)_1(Na)_1(Z)_2$

In the same manner as described in Example 1, 8.8 g (0.04 moles) of sodium dichlorocyanurate dissolved in 200 ml of water were reacted with 3.4 g (0.02 moles) of silver nitrate dissolved in 100 ml of water. There was obtained by filtration a white wet product (12.1 g) and after drying at 50°C, there was obtained 7.9 g (yield: 75.31% based on silver) of a white crystalline solid.

Analysis

Calculated for $(Ag)_1(Na)_1(C_3N_3O_2Cl_2)_2$

Available chlorine: 54.05%
Ag : 20.55%

Found

Available chlorine: 48.17%
Ag : 19.72%

EXAMPLE 3

$(Ag)_2(Ca)_1(Z)_4.3H_2O$

To a vessel containing 100 ml of water there was added 1.29 g (0.01 mole) of cyanuric acid, 4.65 g (0.02 moles) of trichlorocyanuric acid and 1.50 g (0.15 moles) of calcium carbonate. The calcium dichlorocyanurate thereby formed dissolved in the water and then 1.70 g (0.01 moles) of silver nitrate dissolved in 50 ml of water was added thereto. A white precipitate immediately formed and it was removed by filtration and dried at 50°C and then at 80°C to give 5.17 g (yield: 94.2% based on silver) of the compound.

Analysis

Calculated for $(Ag)_2(Ca)_1(C_3N_3O_2Cl_2)_4.3H_2O$

Chlorine: 25.83%
Available chlorine: 51.66%
Ag : 19.65%
Ca : 3.65%

Found

Chlorine: 25.26%
Available chlorine: 50.72%
Ag : 19.74%
Ca : 3.32%

Also, the same compound was prepared from dry calcium dichlorocyanurate prepared previously using stoichiometric amounts of the reactants, that is, without using an excess of calcium salt as was employed in the preceding experiment of this example. Thus, to 4.88 g (0.01 mole) of calcium dichlorocyanurate hydrate dissolved in 100 ml of water, there was added 1.70 g (0.01 mole) of silver nitrate dissolved in 50 ml of water. After filtering and drying the precipitate at 50°C and then at 80°C, there was obtained 4.92 g (yield: 89.61% based on silver) of product containing 49.78% available chlorine.

EXAMPLE 4

$(Ag)_2(Ba)_1(Z)_4.3H_2O$

In the same manner as described above, to 5.31 g (0.01 moles) of barium dichlorocyanurate dissolved in 150 ml of water, was added 1.70 g (0.01 mole) of silver nitrate dissolved in 50 ml of water. The reaction mixture is filtered, then dried at 50°C and then at 90°–100°C to give 5.53 g (yield: 92.48% based on silver) of a white crystalline solid containing 44.03% availble chlorine. Calculated for $(Ag)_2(Ba)_1(Z)_4.3H_2O$ available chlorine is 47.47%.

EXAMPLE 5

For illustrative, but not restrictive purposes, this example describes a specific practical mode of use of a compound according to the invention, wherein the compound is deposited on a porous solid support at a suitable concentration.

To a vessel containing 0.0472 g of potassium dichlorocyanurate dissolved in 500 ml of water, there was added 100 g of Celite. To the resulting suspension there was added 0.017 g of silver nitrate dissolved in 100 ml of water, over a period of 10 minutes, with stirring. Stirring was continued for one additional hour, and then the resulting solid was filtered and dried at 50°C.

A formulation consisting of 0.05 wt.% of $(Ag)_1(K)_1(Z)_2$ supported on Celite was obtained. Such formulation had the same algicidal effect as the corresponding pure active product (Example 1). No algae development was observed when the formulation was applied in a concentration of 5 p.p.m., based on the active ingredient, on a culture of Chlorella vulgaris, in a 100 ml test tube, stirred with aeration, and containing 5 ml of a standard suspension of 120,000 algae/ml.

On the other hand, a concentration of 10 p.p.m., based on the active ingredient killed the algae and produced discoloration of the medium after 48 hours, when applied on 100 ml of a suspension containing 120,000 cells/ml.

The embodiments of this invention in which an exclusive property or privilege is claimed are defined as follows:

1. A chlorocyanurate silver complex having the formula

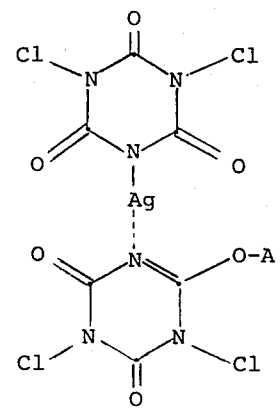

I wherein A is sodium or potassium.

2. A chlorocyanurate silver complex having the formula

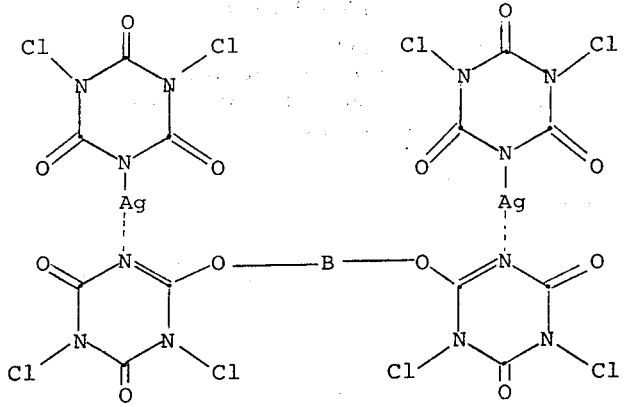
II
wherein B is calcium, barium or magnesium, and hydrates thereof.
3. A complex as claimed in claim 1 in which A is sodium.
4. A complex as claimed in claim 1 in which A is potassium.
5. A complex as claimed in claim 2 in which B is calcium.
6. A complex as claimed in claim 2 in which B is barium.
7. A complex as claimed in claim 2 in which B is magnesium.
* * * * *